(12) United States Patent
Park

(10) Patent No.: US 9,883,871 B2
(45) Date of Patent: Feb. 6, 2018

(54) SPARSE CONTACT TIBIA JIG MECHANISM

(71) Applicant: Somersault Orthopedics Inc., Pleasanton, CA (US)

(72) Inventor: Ilwhan Park, Walnut Creek, CA (US)

(*) Notice: Subject to any disclaimer, the term of this patent is extended or adjusted under 35 U.S.C. 154(b) by 351 days.

(21) Appl. No.: 14/820,424

(22) Filed: Aug. 6, 2015

(65) Prior Publication Data

US 2016/0038159 A1    Feb. 11, 2016

Related U.S. Application Data

(60) Provisional application No. 62/034,073, filed on Aug. 6, 2014, provisional application No. 62/034,085, filed on Aug. 6, 2014.

(51) Int. Cl.
*A61B 17/58* (2006.01)
*A61B 17/60* (2006.01)
*A61F 2/08* (2006.01)
*A61B 17/15* (2006.01)

(52) U.S. Cl.
CPC ............................... *A61B 17/157* (2013.01)

(58) Field of Classification Search
CPC combination set(s) only.
See application file for complete search history.

(56) References Cited

U.S. PATENT DOCUMENTS

2013/0123789 A1*  5/2013  Park .................. A61B 17/15
                                                         606/88

* cited by examiner

*Primary Examiner* — Sameh Boles
(74) *Attorney, Agent, or Firm* — Stephen E. Zweig

(57) ABSTRACT

A tibia cutting jig mechanism (TCJM) is provided having a number N1 of spaced apart TCJM contact points that correspond to a number N1 of spaced apart knee contact points on at least one of a tibia plateau surface and a tibia shaft surface. The TCJM contact points are positioned in contact with the tibia contact points, and a cut bar guide is positioned in contact with the TCJM to provide a location and an angular orientation of a cut bar plane that is to be used to resection and remove a selected portion of the patient's tibia. The TCJM is removed from the patient's knee, and a selected portion of the patent's tibia is resectioned and removed. The number N1 is at most about seven in some embodiments.

22 Claims, 11 Drawing Sheets

SPARSE CONTACT TIBIA JIG MECHANISM

RELATED APPLICATIONS

This application claims priority under 35 U.S.C. § 119 from U.S. provisional application No. 62/034,073 entitled "SPARSE CONTACT TIBIA JIG MECHANISM," filed on Aug. 6, 2014, the entire contents of which are fully incorporated by reference herein for all purposes. This application also claims priority under 35 U.S.C. § 119 from U.S. provisional application No. 62/034,085 titled "METHOD FOR CREATING A CUSTOMIZED ARTHROPLASTY RESECTION GUIDE UTILIZING TWO-DIMENSIONAL IMAGING," filed on Aug. 6, 2014, the entire contents of which are fully incorporated by reference herein for all purposes.

TECHNICAL FIELD

Aspects of the present disclosure relate to orthopedic procedures for knee replacement.

BACKGROUND

Traumatic knee injuries, such as ligament tears and meniscus tears, degenerative joint diseases, such as arthritis, and overall wear and tear can lead to repairing or replacing a knee joint—referred to as an "arthroplasty" procedure. A conventional arthroplasty procedure involves remodeling, realigning and, in some instances, the replacement of the damaged knee joint with prosthetic implants. For example, in a total knee replacement procedure, a portion of the femur and tibia, where they come together at the knee joint, are removed and replaced with a femoral shell and a mating tibial plate, respectively, that together function like a healthy knee joint.

To assist in arthroplasty procedures, and particularly partial or total knee replacements, a jig may be used to position any one of a number of possible instruments used to drill, cut, and shape or otherwise operate on the damaged knee area. In the particular case of a total knee replacement, a jig may be positioned on the femur to mount a cutting guide that in turn supports a bone saw or other tool to cut (resect) a portion of the distal region of the femur. Similarly, a jig may be positioned on the tibia to mount a cutting guide that in turn supports a bone saw or other tool to resect a portion of the proximal region of the tibia. After the femur and tibia are prepared, the surgeon mounts the femoral shell and tibial plate.

Images of orthopedic joints that are candidates for partial or total replacement are often formed as MRI images, referred to here as "slices," with each such image being a projection on a two dimensional image forming substrate. Each such MRI image is actually a three dimensional "voxel," representing a thickness of approximately 2 mm of partial images of cortical bone, cancellous bone cartilage and open space, with each such material having its own range of grey scales in the MRI image. For a full three dimensional representation of an anatomical surface of interest, it is often necessary to obtain tens to hundreds of MRI slices in each of three views (coronal or front view, axial or top view, and sagittal or side view) for a given anatomical component.

Many of the knee replacement procedures presently use what is characterized as "full segmentation" in order to represent a relevant portion of a femur surface or a tibia surface in three dimensions. This approach requires use of a dense, three dimensional grid of points to accurately represent a surface, especially a surface having cusps or sharp corners with very small associated radii of curvature. This approach has several disadvantages, including the following: (1) this approach may be time consuming, often requiring 4-20 hours of intense numerical work to generate and check the accuracy of the grid point coordinates for a single surface; (2) because of the time required to implement this approach for a single surface, use of this approach in mass manufacturing of custom or semi-custom instruments is limited; (3) this approach may introduce geometrical errors, including closing errors; (4) because of the close spacing of grid points, polynomials of high mathematical degree are used, which can introduce undesirable "ripples" in the mathematical surface produced by a full segmentation process; and (5) formation and analysis of a large number of MRI slices is required.

It is with these observations in mind, among others, that various aspects of the present disclosure were conceived.

SUMMARY

Aspects of the present disclosure involves a cutting jig for positioning a tibia cutting tool on a tibia including a first and a second intercondylar tubercle with a spine therebetween, a first articular region adjacent the first intecondylar tubercle and a second articular region adjacent the second intercondylar tubercle, the tibia further including a tibia shaft. The cutting jig may include a substrate or other apparatus or structure that includes a plurality of jig contact points. For example, the substrate may include:

a first jig contact point oriented to contact the tibia anterior of the spine when the jig is positioned on the tibia for a procedure;

a second jig contact point oriented to contact the first articular region of the tibia when the jig is positioned on the tibia for a procedure;

a third jig contact point oriented to contact the first articular region of the tibia when the jig is positioned on the tibia for a procedure, the second jig contact point proximate the first jig contact point;

a fourth jig contact point oriented to contact the second articular region of the tibia when the jig is positioned on the tibia for a procedure; and a fifth jig contact point oriented to contact the second articular region of the tibia when the jig is positioned on the tibia for a procedure, the fifth jig contact point proximate the fourth jig contact point.

The jig may also include a projection extending from the substrate, the projection including:

a sixth contact point oriented to contact the tibia shaft when the jig is positioned on the tibia for a procedure; and a seventh contact point oriented to contact the tibia shaft when the jig is positioned on the tibia for a procedure, the seventh contact point proximate the sixth contact point.

The jig may also include a cut guide, which may be integrated with the substrate or be provided by a cutting guide attached thereto that provides the cut guide, which may be in the form of a slot or other mechanism by which a surgeon may resect the femur along an established cut plane transverse the femoral axis and typically associated with a partial or total knee replacement procedure.

DETAILED DESCRIPTION

Figure 1A:
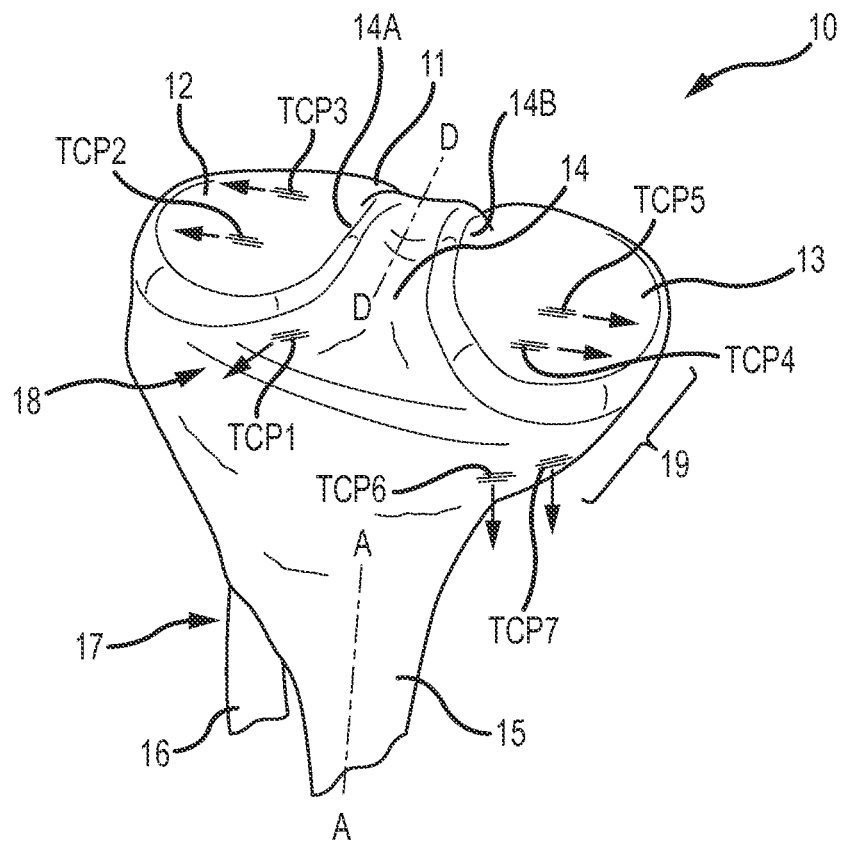
FIGS. 1A and 1B are isometric views of a proximal portion of a tibia (right knee), indicating tibia contact points for a tibia cutting jig mechanism.

It would be desirable to eliminate the full segmentation process and the associated three dimensional anatomical modeling of a tibia surface, among other things; and to replace this approach with data obtained from relatively few MRI "slices," as few as five, for example, two-dimensional slices, that permits flexibility in choice of contact points between the tibia surface and the instrument (jig) that facilitates resectioning and removal of a portion of the knee component. It would also be desirable to replace the full segmentation procedure, with its thousands of grid points, with a simpler, quicker procedure that works with as few as about seven contact points between the anatomical surface and resectioning mechanism for the tibia component. Aspects of the present disclosure may involve a "sparse contact" approach that provides a cutting jig mechanism, which defines a cut plane for a tibia component of a knee.

A proximal, upper portion, of a tibia component 10, illustrated in FIGS. 1A and 1B for a right knee, a tibia table 11 having one or two concave surfaces 12, 13, a tibial spine 14 and intercondylar tubercles 14A, 14B separating these surfaces as a tibia top surface, having a tibia shank 15 that extends below the top surface, and having a fibula 16 for stability that extends roughly parallel to the tibia shank. Interest focuses here on the tibia top surface and on an upper portion of the tibia shank.

Figure 1B:
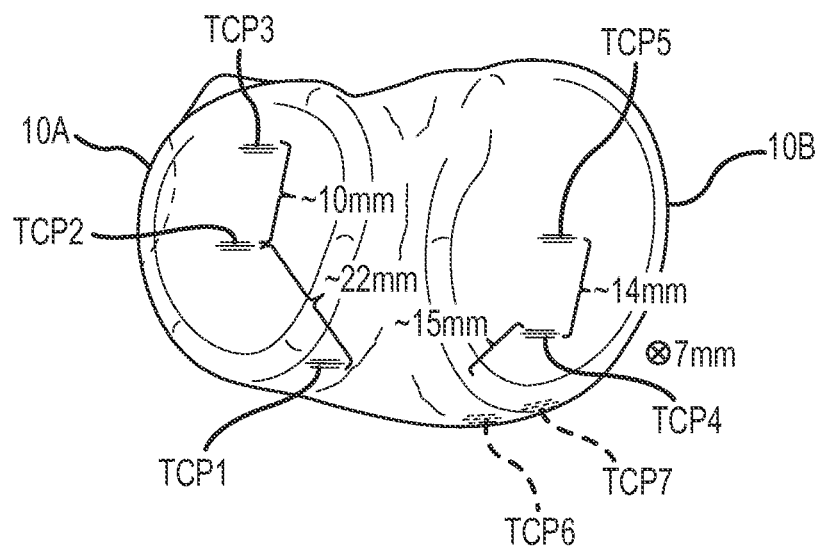
Figure 2A:
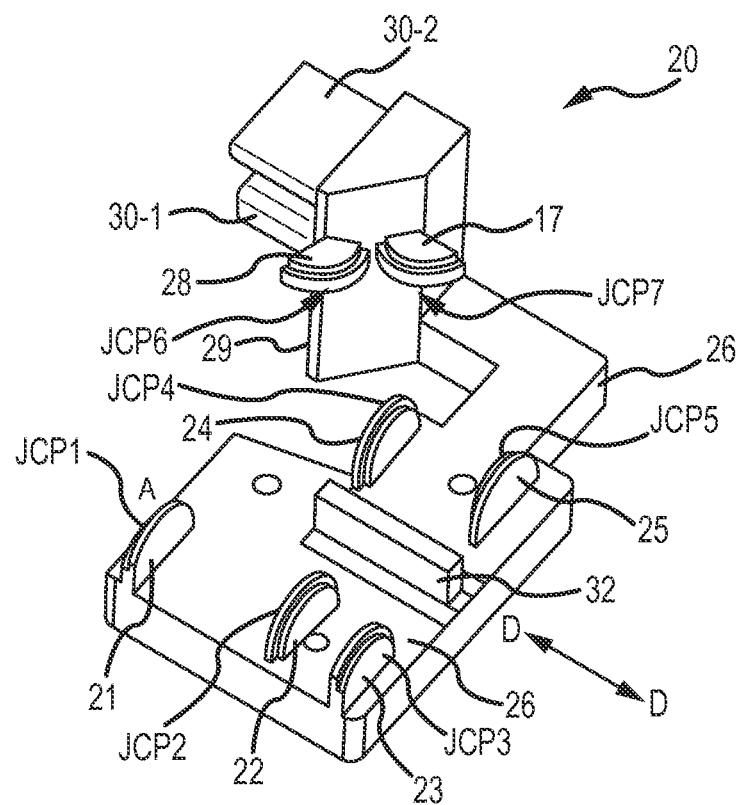
FIGS. 2A and 2B are isometric views of a tibia cutting jig mechanism (TCJM), indicating jig contact points that correspond to the tibia contact points in FIGS. 1A and 1B.
Figure 2B:
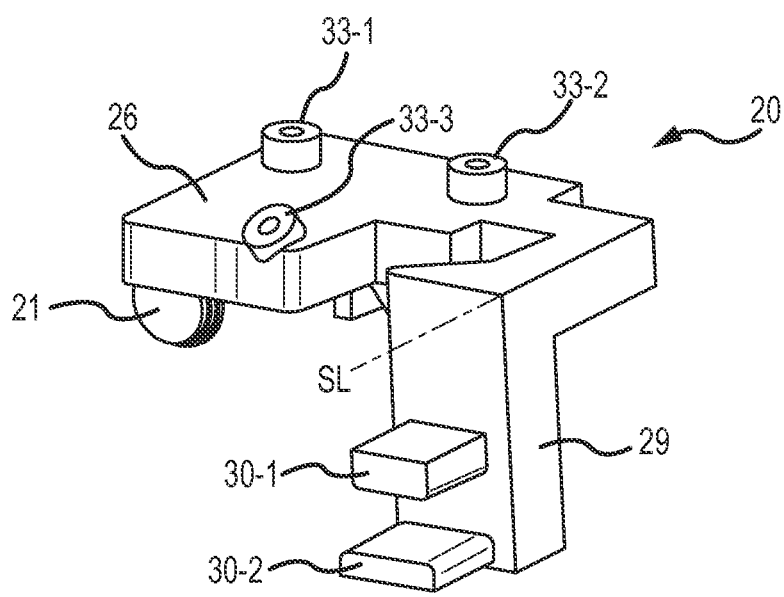

A tibia cutting jig mechanism (TCJM) or simply "jig" 20, illustrated in isometric views in FIGS. 2A and 2B, and in FIGS. 3A-3F showing the jig positioned on or relative to a tibia, has a number (N) of jig contact points (JCP) that make contact with the same number of corresponding points on and adjacent to the top surface of the tibia 10 (FIGS. 1A and 1B), where the number N is as few as seven (7) and may be slightly smaller or slightly larger in some embodiments. The number N used here may be compared with a corresponding number used in the prior art full segmentation approach, which typically involves hundreds to several thousand contacts for a tibia component. The number N used here depends, in part, on placement of the jig contact points on the jig 20 and on placement of the corresponding contact points on the proximal surface of the tibia. The contact points help stabilize the jig 20, even in the small number proposed, against longitudinal, transverse and/or rotational movement relative to the tibia top surface when the jig and the tibia top surface are in contact. For example, when a surgeon is moving the jig onto the tibia in order to secure a cut plane guide 31 CPG (FIG. 3D) to the top area of the tibia, in order to resect the tibia before applying a prosthetic as part of a total knee replacement, it is important for the jig to be stably positioned on the tibia prior to pinning.

The jig 20 is positioned in contact with the top surface of the tibia 10 and oriented to properly position the cut plane guide 31. The jig, once positioned correctly, is pinned to the tibia by inserting three pins (not shown) through three corresponding bosses (33-1, 33-2, 33-3) projecting from the jig and defining apertures through which the pins are inserted. It may be necessary to predrill the femur, possibly using the bosses or drill guides, prior to placement of the pins. The cut plane guide 33 is mounted between two projections 30-1 and 30-2. The guide 31 is pinned to the tibia through two cut bar positioning apertures, CBA1 and CBA2, shown in FIG. 3D and defined in the cut plane guide. Two positioning pins securing the bar may be drilled into a portion of cortical bone (tibia below the tibial plateau) of the patient, taking care not to extend drilling of either of the apertures, CBA1 and CBA2. The jig 20 is then removed, leaving the guide 31 in place to provide a guide for resectioning and removal of an upper portion of the patient's tibia, for replacement of this component of the knee. As illustrated, the guide 31 defines a saw slot 35 that may receive and guide a bone saw for the resectioning procedure. After resectioning has occurred, the cut plane guide is removed and optionally can be reused in replacement of another patient's knee.

The "sparse contact" approach discussed here relies on a small number (e.g., five or fewer) of two dimensional MRI images or "slices" of the tibia, with each slice containing or illuminating one or two contact points between the anatomical surface (tibia) and the tibia cutting jig mechanism that helps define a cut plane position for resectioning and removing a portion of part of the tibial area of interest. This approach has one or more advantages: (1) the number of MRI slices used to identify femoral contact points for corresponding jig contact points is quite small (e.g., at most about five) and represents no more than about 5-10 percent of the total volume of the portion of the anatomy component of interest; (2) the number of contact points and associated coordinates needed for position stability of the jig is also small (e.g., at most about seven, as compared with hundreds to thousands for a full segmentation approach); (3) the "design time" required to determine relevant component dimensions and coordinates of the contact points on the anatomical surfaces of the tibia is estimated to be about 20 minutes and is expected to decrease further as one accumulates experience in the dimensioning process; (4) this "sparse contact" approach will permit semi-custom design and fabrication of the knee replacement components and associated tools; and (5) this approach provides some flexibility for the orthopedic surgeon to exercise creativity and compensation in choices and modifications of some of the dimensions.

A tibial cutting jig 20 conforming with various aspects of the present disclosure includes a substrate from which various jig contact points (JCPm) project, are otherwise supported or defined. In one possible implementation, the jig 20 is a unified structure formed from a block of base material using a computer numerical control (CNC) machine. However, it is possible for the jig to be an assembly of various components to form the final cutting jig structure. Alternatively, the jig may be created through molding, machining, milling, forming, 3D printing, assembling, or other processes. The term "substrate" as used herein is meant to refer to a base structure upon which the various jig contact points and jig contact point supporting structures are provided or otherwise supported, and by which the relative positioning of the various jig contact points are maintained. As mentioned, the jig may be a unified structure and hence the substrate and jig contact points are formed from the same material and thus the relative positioning of the jig contact points is naturally maintained. Other processes, such as milling a base material or forming a jig in a mold, would provide a similar unified structure. It is not necessary, however, that the jig be unified structure in which case the substrate may be a frame or other structure or assembly on which various jig contact point defining structures are attached or otherwise associated.

The jig contact points are arranged and spaced such that a surgeon may press the jig onto the proximal surface of the tibia and the jig will be properly positioned when the jig contact points are seated on respective tibial contact points (TCPm). Notably, there are a discrete number of jig contact points (e.g., 5-8) as opposed to full surfaces or far more numerous numbers of contact locations. The jig also includes a cutting guide support structure onto which the cutting guide 31 may be mounted. When the jig 20 is seated on the tibia 10, the jig may be pinned to the tibia and properly position the cutting guide so that a resection of the tibia may be performed pursuant to a total knee replacement, for example.

The tibia plateau 11 at a proximal surface of the tibia 10, shown in FIGS. 1A and 1B, includes a concave first region 12, a second region 13, which may be concave (depressed), be partly or wholly "flat," or be convex, spaced apart from the first region 12. As shown, both the first and second region, which may also be referred to as the superior articular surfaces of the lateral 10A and medial 10B tibial condyles, respectively, are both slightly concave. The tibial spine 14, lying between intercondylar tubercles (14A, 14B), with an associated spine direction D-D, is located between and spaced apart from the first region 12 and the second region 13. The tibia shaft 15 extends downward (distally) along a tibia axis A-A from the tibia plateau 11. The fibula 16, which provides stability for the tibia, is connected at its proximal end 17 to the tibia 10 at the articular facet, which is near but below the tibia plateau 11 on the lateral condyle. Several tibia contact points, TCPm (m=1, 2, M; M≈7) are identified in FIGS. 1A and 1B on or near the tibia plateau 11, in the first region 12 (m=1, 2)), in the second region (m=3, 4), and in a third region 18 adjacent to and anterior from the spine 14 (m=5) in an intercondylar area at the anterior of the tibia plateau. One or two other tibia contact points (m=6, 7) are identified on an upper surface of the tibia shank 15, approximately 1 cm below the tibia plateau 11, and on the medial tibial condyle 10B. Additional contact points may be included but would not contribute substantially to stability of the tibia cutting jig mechanism 20, when fitted against the tibia 10.

Figure 3A:
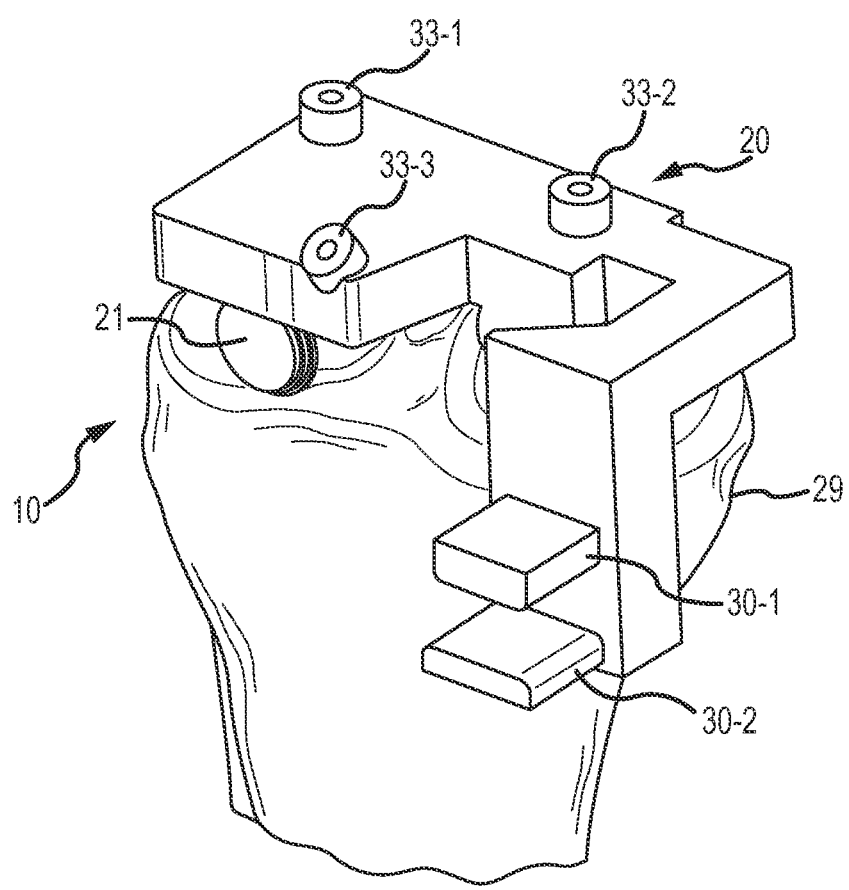
FIGS. 3A-3C and 3E are views of a tibia with a jig pressed thereon.
Figure 3B:
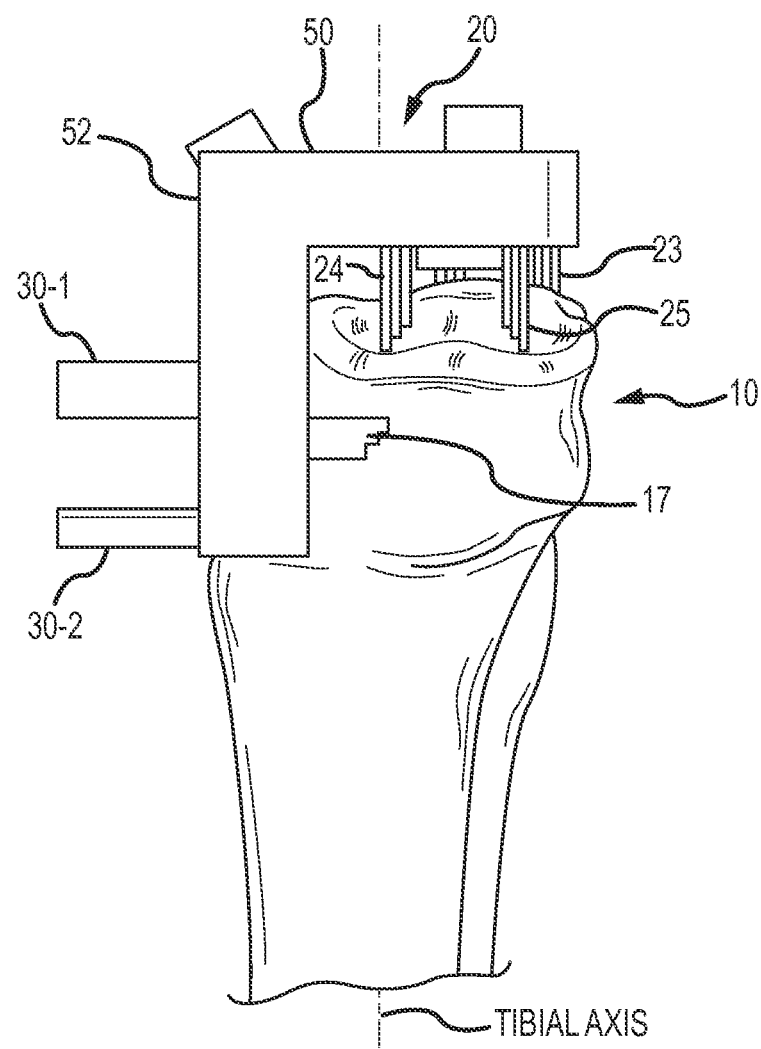
Figure 3C:
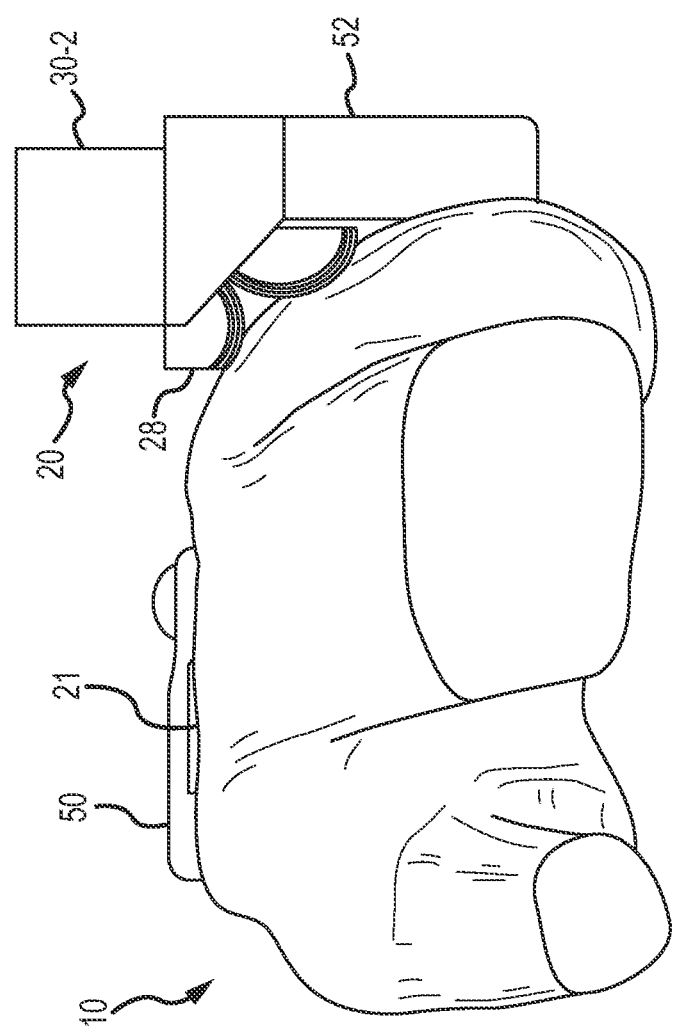

FIGS. 2A and 2B are isometric views of an embodiment of the jig 20, and FIGS. 3A-3F are various views of the jig in relation to the tibia 10. The jig includes a first substrate portion 50 and a second substrate portion 52 generally perpendicular to the first substrate portion. As can be seen in FIG. 3B and elsewhere, the first substrate portion 50 is generally transverse to the tibial axis A-A of the tibia (substantially in the axial plane when mounted) and the second substrate portion 52 is generally perpendicular to the first substrate portion. It should be noted that the jig positions the cut plane bar 31, and hence the jig position on the tibia will vary based on the anatomy of the patient, the type of procedure, the type of prosthetic, and any number of other factors. Hence, the anatomical relationships described are illustrative and not limiting. Further, the jig structure illustrated is a convenience of manufacturing, with the jig originally formed from a block of material and machined away to form the resulting structures. Thus, it is not necessary that the first substrate portion be perpendicular to the second portion, for example. It is possible to machine these structures more or less so long as the resulting jig contact points are formed, and there are not obstructions to positioning the jig on the tibia properly. Moreover, different shapes (besides the partial circles shown) may be used to form the surfaces providing the jig contact points.

Figure 3D:
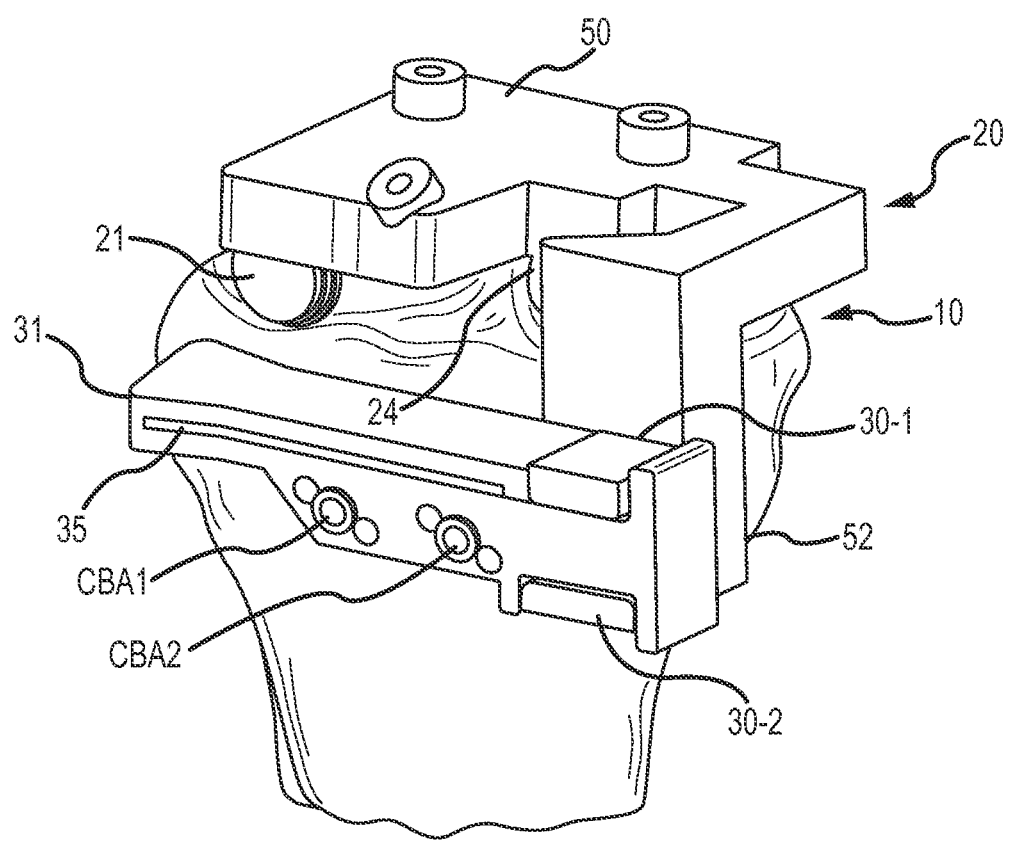
FIG. 3D is a view of the jig pressed on the tibia and with a cut plane guide on the jig.
Figure 3E:
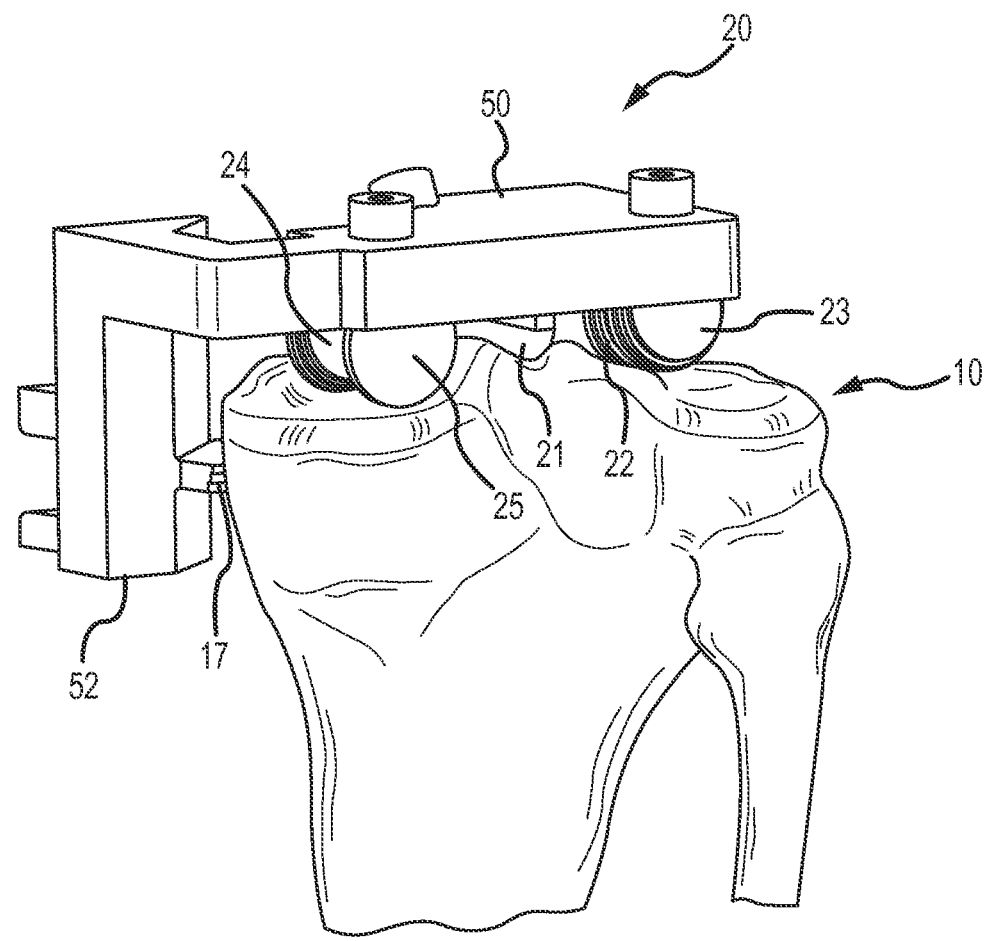

Five curvilinear surfaces, 21, 22, 23, 24, 25, project from a first substrate surface 26 of the jig 20 to provide jig contact points, JCPm (m=1, 2, . . . , 5) corresponding to the respective tibia contact points, TCPm (m=1, 2, . . . , 5) (FIGS. 1A-1B). One or two additional jig contact points JCPm (m=6, 7) are provided by curvilinear surfaces, 27 and 28, which correspond to the respective tibia contact points TCP6 and TCP7. It is possible to use fewer contact points on the tibia surface, and to use one or no contact points below the surface, or to use an additional point or two below the surface. In the implementation shown, the curvilinear surfaces are in the form of sectors (partial circles with a radius). The surfaces 27 and 28 project from a vertically oriented polygonal structure 29 defined by the second substrate portion 52. The polygonal structure 29 provides regions of attachment support for the first and second, spaced projecting plates, 30-1 and 30-2, that define the cut plane guide support for the cut guide 31 (FIG. 3D). While two plates are shown, one plate may suffice and other forms of members may also serve as features whereby a cut plane support is mounted. The placement of the surfaces and respective contact points JCP6 and JCP7 provide stability when the CPG 31 is being pinned to the bone due to the position of the contact points TCP6, TCP7 on the jig contact points JCP6, JCP7 formed by projections 28 and 29 from the second substrate and facing the bone.

As shown, some of the curvilinear surfaces are formed of a plurality of curvilinear surfaces (e.g., sectors) arranged proximate each other and forming radial steps of increasing (or decreasing) radiuses depending on perspective. The collection of radial steps of any given projection provides greater structural integrity of the projection due to the thickness of the projection. The contact point for any given projection, however, may be defined along only one of the radial steps and preferably the largest radius step in the example jig implementation shown here. Moreover, it is possible to provide a larger projection, without any steps, one or more steps of differing thicknesses, depending on the particular contact point being defined as well as the contour and surface shape of the tibia at the tibial contact point for the corresponding jig contact point. The use of steps, however, helps ensure that any of the contact points touch the bone while also maintaining structural support for the projection due to the increasing thickness at and below the steps.

A linear sight projection 32, projecting from the substrate surface 26 and located between the jig contact points, JCP1, JCP2 and JCP3, and the jig contact points, JCP4 and JCP5, serves to align itself with the spine direction D-D defined by the spine aperture (FIG. 1A) when the jig is properly positioned on the tibia. Hence, a surgeon may use the sight 32 to visually align the jig relative to the intercondylar tubercles 14A, 14B and the spine 14 therebetween. In the specific jig shown, the central vertical projection, as well as other features discussed herein, may be formed by tooling elements, such as from a CNC machine router bits. Adjacent the projection and in the space between the surfaces 21, 22, 23, 24 and 25, material may be removed to allow a surgeon to see past the vertical projection to where the points along the various curvilinear surfaces contact the respective tibial contact points as discussed herein.

FIGS. 4A through 4I illustrate two dimensional, linear and curvilinear formats that can be used in embodiments to construct tangent lines and other approximation elements (FIG. 4J) used in obtaining relevant dimensions of the upper tibia and corresponding tibia cutting jig mechanism 20 shown in the various figures. Referring first to FIG. 4J, a portion of an MRI slice is illustrated. The MRI slice shows a line 54 denoting a boundary of the tibia, where a tibia contact point 56 is located and where a corresponding jig contact point 58 is defined, which will contact the tibia at the tibia contact point. The tibia portion illustrated may be cortical bone, cancellous bone cartilage at a boundary to open space or otherwise. Since each such material may have its own range of grey scales in the MRI image, the boundary line is merely representative of a contact area, which may not be in fact a discrete line. The tibia contact area of the MRI may be a slice through all or a portion of either or both condyles, the shank, or other regions of the proximal area of the tibia and particularly the tibia plateau relevant to a total knee replacement procedure or other tibial procedure that may take advantage of the jig described herein.

In the view illustrated in FIG. 4J, a portion of a coronal plane MRI slice of the proximal tibia is illustrated. More specifically, the boundary line 54 represents a coronal plane MRI slice of the lateral condyle encompassing the tibia contact point 56. In order to define a jig contact point, various lines and geometrical shapes may be deployed. The curve, $y=f(x)$ shown in an example in FIG. 4J is assumed to be continuously differentiable in an interval $a<x<b$, and to have a well-defined tangent line slope 60, $dy/dx=df/dx$, at a point, $(x, y)=(x0, y0)$. For example, three spaced apart, noncollinear coordinate pairs, $(xm, ym)$ ($m=1, 2, 3$) can be used to determine an optimal circle (center and radius) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the tibia contact area of interest. In the case of a circular contact point-defining structure or other structures, the structure may be made to intersect or touch the tibia contact area of interest at and with coinciding tangent lines.

Figure 4A:
FIGS. 4A-4I illustrate one- and two-dimensional, closed and open, linear and curvilinear formats that can be used to construct tangent lines and other linear and curvilinear approximation elements used in obtaining relevant dimensions for surfaces defining jig contact points in different embodiments of the invention, illustrated in one example in FIG. 4J.

In the case of FIG. 4A, a rectangle is used to define the jig contact point at the corresponding femoral contact point. The line defined by the MRI slice encompassing the femoral contact point is characterized by a curve, $y=f(x)$, which is assumed to be continuously differentiable in an interval $a \leq x \leq b$, and to have a well-defined tangent line slope, $dy/dx=df/dx$, at a point, $(x, y)=(x0, y0)$. For example, three spaced apart, noncollinear coordinate pairs, $(xm, ym)$ ($m=1, 2, 3$) can be used to determine an optimal rectangle (length and width) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a rectangular contact point defining structure or other structures, the structure may be made to intersect or touch the femoral contact area of interest at and with coinciding tangent lines.

Figure 4B:

In the case of FIG. 4B, a line segment is used to define the jig contact point at the corresponding femoral contact point. The line defined by the MRI slice encompassing the femoral contact point is characterized by a curve, $y=f(x)$, which is assumed to be continuously differentiable in an interval $a \leq x \leq b$, and to have a well-defined tangent line slope, $dy/dx=df/dx$, at a point, $(x, y)=(x0, y0)$. For example, three spaced apart, noncollinear coordinate pairs, $(xm, ym)$ ($m=1, 2, 3$) can be used to determine an optimal line (length) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a linear contact point defining structure or other structures, the structure may be made to intersect or touch the femoral contact area of interest at and with coinciding tangent lines.

Figure 4C:
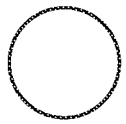

In the case of FIG. 4C, a circle is used to define the jig contact point at the corresponding femoral contact point. The line defined by the MRI slice encompassing the femoral contact point is characterized by a curve, $y=f(x)$, which is assumed to be continuously differentiable in an interval $a \leq x \leq b$, and to have a well-defined tangent line slope, $dy/dx=df/dx$, at a point, $(x, y)=(x0, y0)$. For example, three spaced apart, noncollinear coordinate pairs, $(xm, ym)$ ($m=1, 2, 3$) can be used to determine an optimal circle (center and radius) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of a circular contact point defining structure or other structures, the structure may be made to intersect or touch the femoral contact area of interest at and with coinciding tangent lines.

Figure 4D:

In the case of FIG. 4D, an ellipse is used to define the jig contact point at the corresponding femoral contact point. The line defined by the MRI slice encompassing the femoral contact point is characterized by a curve, $y=f(x)$, which is assumed to be continuously differentiable in an interval $a \leq x \leq b$, and to have a well-defined tangent line slope, $dy/dx=df/dx$, at a point, $(x, y)=(x0, y0)$. For example, three spaced apart, noncollinear coordinate pairs, $(xm, ym)$ ($m=1, 2, 3$) can be used to determine an optimal ellipse (center and radius) (1) that is coincident with the curve, $y=f(x)$, at each of the locations $(xm, ym)$ or (2) that has the same tangent line slope as the function $y=f(x)$ at one or more of the locations $(ym, ym)$. In general, a jig contact point may be defined at a point or region along the curve $y=f(x)$ defining the femoral contact area of interest. In the case of an elliptical contact point defining structure or other structures, the structure may be made to intersect or touch the femoral contact area of interest at and with coinciding tangent lines.

Figure 4E:

In the case of FIG. 4E, a triangle is used to define the jig contact point at the corresponding femoral contact point. The line defined by the MRI slice encompassing the femoral contact point is characterized by a curve, $y=f(x)$, which is assumed to be continuously differentiable in an interval $a \leq x \leq b$, and to have a well-defined tangent line slope, $dy/dx=df/dx$, at a point, $(x, y)=(x0, y0)$. For example, three spaced apart, noncollinear coordinate pairs, $(xm, ym)$ ($m=1, 2, 3$) can be used to determine an optimal triangle (base and height) (1) that is coincident with the curve, $y=f(x)$, at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a triangular contact point defining structure or other structures, the structure may be made to intersect or touch the femoral contact area of interest at and with coinciding tangent lines.

Figure 4F:

In the case of FIG. 4F, a trapezoid is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal trapezoid (base and height) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a trapezoidal contact point defining structure or other structures, the structure may be made to intersect or touch the femoral contact area of interest at and with coinciding tangent lines.

Figure 4G:

In the case of FIG. 4G, a parallelogram is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal parallelogram (base and height) (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a parallelogram contact point defining structure or other structures, the structure may be made to intersect or touch the femoral contact area of interest at and with coinciding tangent lines.

Figure 4H:

In the case of FIG. 4H, a quadratic curve is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal quadratic curve (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a quadratic curve contact point defining structure or other structures, the structure may be made to intersect or touch the femoral contact area of interest at and with coinciding tangent lines.

Figure 4I:
Figure 4J:
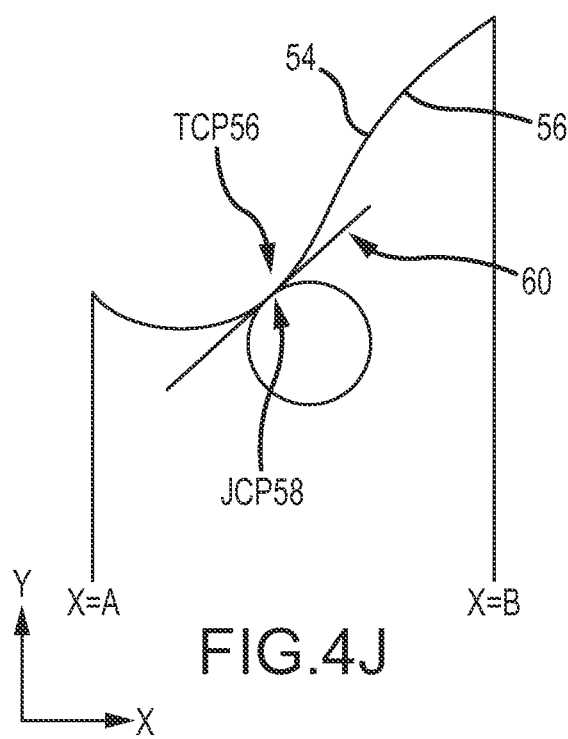

In the case of FIG. 4I, a cubic curve is used to define the jig contact point at the corresponding femoral contact point. The line defined by the MRI slice encompassing the femoral contact point is characterized by a curve, y=f(x), which is assumed to be continuously differentiable in an interval a≤x≤b, and to have a well-defined tangent line slope, dy/dx=df/dx, at a point, (x, y)=(x0, y0). For example, three spaced apart, noncollinear coordinate pairs, (xm, ym) (m=1, 2, 3) can be used to determine an optimal cubic curve (1) that is coincident with the curve, y=f(x), at each of the locations (xm, ym) or (2) that has the same tangent line slope as the function y=f(x) at one or more of the locations (ym, ym). In general, a jig contact point may be defined at a point or region along the curve y=f(x) defining the femoral contact area of interest. In the case of a cubic curve contact point defining structure or other structures, the structure may be made to intersect or touch the femoral contact area of interest at and with coinciding tangent lines.

Depending on the implementation, it may be preferable that no corner point, such as a jig contact point, be sharp or otherwise have a high degree of sharpness such as is often associated with a true "point". Rather, a contact point may have an associated point segment that is at least about 0.3 mm in actual size or larger up to and including a line, in one possible implementation. The incorporation of this constraint will help ensure that, for example, a jig contact point will have adequate frictional contact such that the contact point will not slip or otherwise move relative to a region on the tibia, but at the same time the contact point will not penetrate or pierce any soft tissue on the portion of the tibia being contacted and hence possibly distort the fit of the jig to the tibia. It is less of a concern about damaging the tibia as the portion of the tibia being contacted is likely to be removed (resected) and replaced with a prosthetic implant. Notably, where a straight line segment from a square, rectangle, triangle or trapezoid is used as the contact point defining structure, and a corner of such structure is not the contact point, the area along the straight line segment at which contact is made, is considered a contact point. Moreover, in such an implementation, the straight line segment may have a rounded or otherwise non-knife edge cross section, particularly at the area where the surface is intended to contact the femur.

Figure 3F:
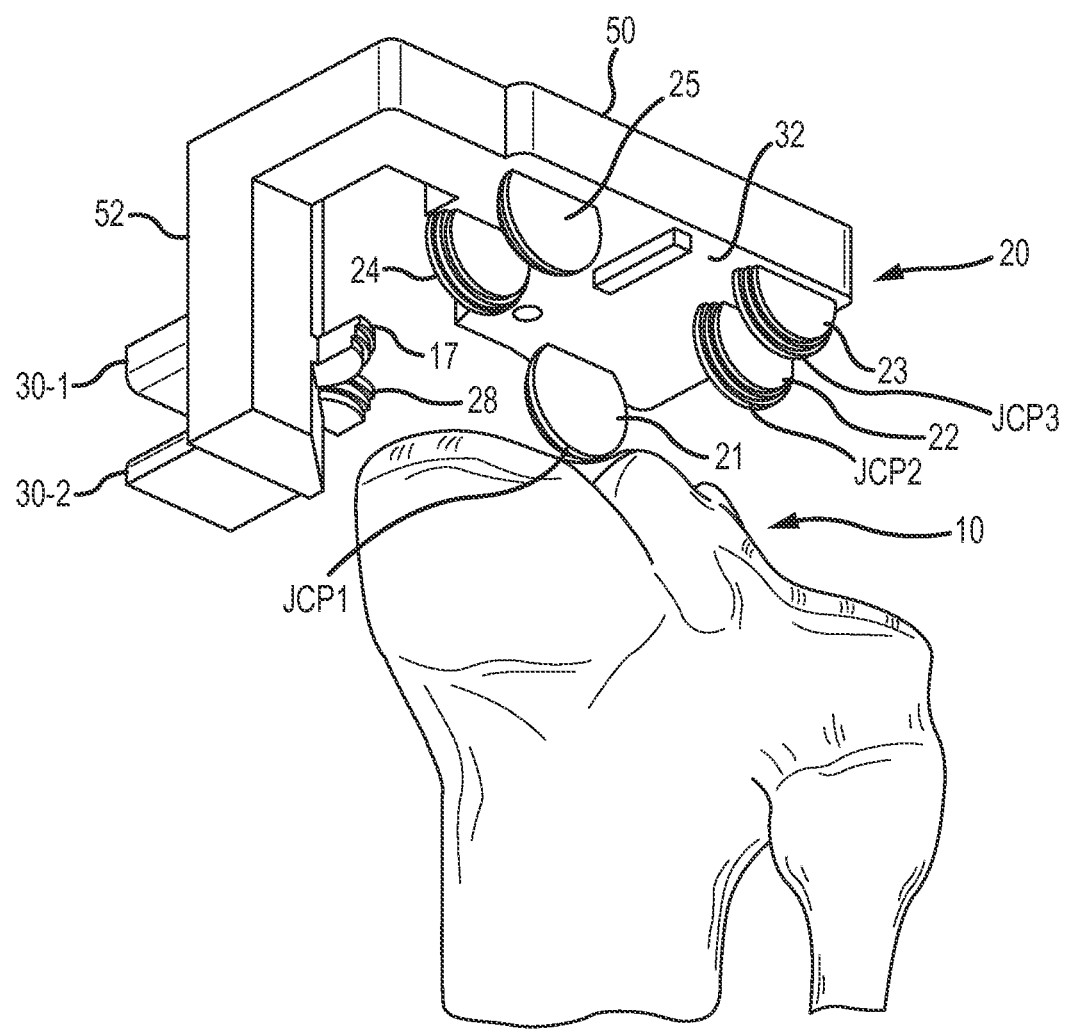
FIG. 3F is a view of the jig proximate but above the tibia.
Figure 5:
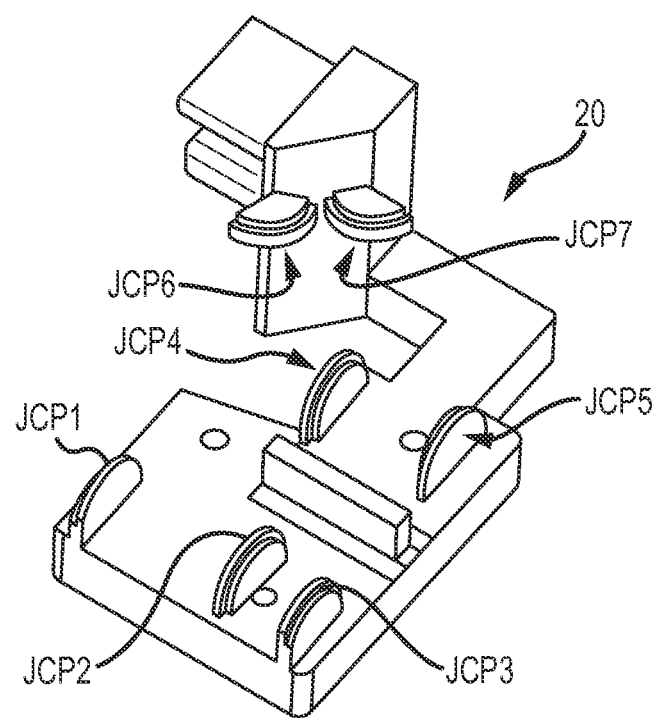
FIG. 5 is an isometric and schematic view indicating suitable locations of a jig defining jig contact points according to an embodiment.

FIGS. 5 and 3F illustrate suitable locations of jig contact points, JCP1, JCP2 and JCP3, for the jig 20, spaced apart by separation distances of approximately 1 cm (JCP2 to JCP3) and 2 cm (JCP1 to JCP2). With respect to JCP2 and JCP3, the separation may be in range, such as between 7 mm and 13 mm, depending on the dimension of the particular tibia to which the jig is built. As shown in this embodiment, the jig contact point JCP2 is located between the jig contact points JCP1 and JCP3 and is closer to the jig contact point JCP3. The three jig contact points JCP1, JCP2 and JCP3 are located on the curvilinear projections 21, 22 and 23 (FIG. 2A), respectively, which are substantially parallel to each other. The various curvilinear projection are shown parallel but they may, of course, be substantially parallel and may vary from parallelism due to manufacturing tolerance, design differences, and the like. Thus, to be substantially parallel, the projections may vary from true parallel by 1-10 degrees. Similarly, design preference or functionality, may dictate that the projections not be parallel where shown. For example, in some instances, the projections may be substantially perpendicular from the movement constricting feature to which the projections are positioned. For example, for contact points JCP2 and JCP3, the respective curvilinear projections may be positioned substantially perpendicular to the slope of the adjacent articular surface that restricts medial movement of the jig. Also, with a larger or smaller sized tibia, or differently spaced and/or shaped condyles and/or surfaces, the contact points may be more or less separated. Moreover, the contact points may be arranged, laterally, medially, anteriorly and/or posteriorly to other locations or as illustrated in the figures. As with other surfaces, projections and the likely structure illustrated is a convenience of manufacturing, with the jig originally formed from a block of material and machined away to form the resulting jig contact points JCP1, JCP2 and JCP3.

In the implementation shown, the curvilinear surfaces 21, 22, and 23 each comprise a plurality of semi-circular portions, each of slightly differing radius (lesser radius). The same situation is also present with the surfaces 24 and 25, and 17 and 28. In each case, the largest radius portion provides the jig contact point and the adjacent portions (steps) of lesser radius enhance the structural integrity of the projection but are not meant to contact the tibia, although some unintended contact is possible. Accordingly, the decreasing radius portions are positioned on the side of the projection best suited to not interfere with the tibia or the jig contact point. For example, with respect to surfaces 24 and 25, the decreasing radius portions of each surface face each respective surface. The tibia in the area where the jig contacts the tibia at tibia contacts points TCP4 and TCP5, however, is concave. Accordingly, the radiuses do not track the slope of the tibia in the contact area, but instead are counter to the slope, thereby minimizing the likelihood of inadvertent contact. In contrast, if the decreasing radius portions were placed on the opposite sides shown, the decreasing radiuses would be similar to the upward slope of the tibia in these areas and while they may not contact the tibia, the decreasing radiuses would have less of a distance and thus more possibly contact the tibia.

FIGS. 5, 3B and 3F, and others illustrate suitable locations of jig contact points, JCP4 and JCP5, for the jig 20, spaced apart by a separation distance of approximately 1 cm (or in a range of 7 mm to 13 mm, although others ranges are possible), as shown. The two jig contact points, JCP4 and JCP5, are located on the curvilinear sector projections 24 and 25 (FIG. 2A), respectively, which are substantially parallel to each other. Each of the jig contact points, JCP1, JCP2, JCP3, JCP4 and JCP5, can move in one direction in a plane of the tibia plateau 11 (indicated by arrows in FIG. 1A) but cannot move in an opposite direction (see FIG. 6) because of presence of solid features that are part of the topography of the tibia plateau 11. With a larger or smaller sized tibia or differently spaced and/or shaped condyles and/or articular surfaces, the contact points may be more or less separated. Moreover, the contact points may be arranged, laterally, medially, anteriorly and/or posteriorly to where illustrated.

The curvilinear projections illustrated may define sectors with the contact point defined along the edge of the sector. In the implementation illustrated, the projections extend from the substrate as discrete planar elements with the surface intended to contact the tibia defining the sector. As discussed, the edge may define a stepped structure in one possible example. Moreover, the edge may define a relatively narrow flat edge so as not to define a sharp edge. Other suitable shapes may be used to define the contact points. For example, a conical projection with the contact point defined as the tip area of the cone may extend from the substrate. In another example, a post may extend from the substrate, with the tip area of the post defining the jig contact point. The tip may be rounded, flat, beveled, etc. Other planar shapes, such as those illustrated in FIGS. 4A-4I, may also be used, with an edge of the planar shape including the contact point.

FIGS. 5, 6, 3B, 3C, and 3E illustrate suitable locations of jig contact points, JCP6 and JCP7, for the jig 20, spaced apart by a separation distance of approximately 1 cm, as shown (measured from the respective contact points). The two jig contact points, JCP6 and JCP7, are located on the curvilinear sector projections 28 and 27 (FIG. 2A), respectively, and are substantially coplanar. Each of the jig contact points, JCP6 and JCP7, can move downward (indicated by arrows in FIG. 1A) along the tibia shank axis A-A, but cannot move upward because of presence of a solid object, the upper portion 19 of the tibia, when the jig is properly positioned with points JCP6 and JCP7 contacting the tibia at TCP6 and TCP7.

The contact points JCP1, JCP2, JCP3, JCP4 and JCP5 are associated with features of the tibia plateau 11, and the jig contact points JCP6 and JCP7 are associated with features of the shaft. One goal of the contact points on the jig 20 is to provide an optimal position of the jig in contact with the proximal tibia, for which lateral rotation (posterior to anterior, or anterior to posterior) of the jig relative to the tibia, or longitudinal (sagittal) translation of the jig relative to the tibia, or axial twisting (rotation) clockwise or counterclockwise, is resisted by friction caused by contact between the jig and the tibia at the contact point. Stated differently, when the jig is properly positioned on the tibia such that the jig contact points are touching the respective tibial contact points and firmly seated there by a surgeon, the jig is firmly held in the correct orientation on the tibia through the interoperation of the jig contact points to the tibia contact points. While it is possible that a small number of the jig contact points, e.g., one or two, may not actually touch the tibia due to actual tibial inconsistencies relative to the images of the tibia, the jig will nonetheless be held in position.

Figure 6:
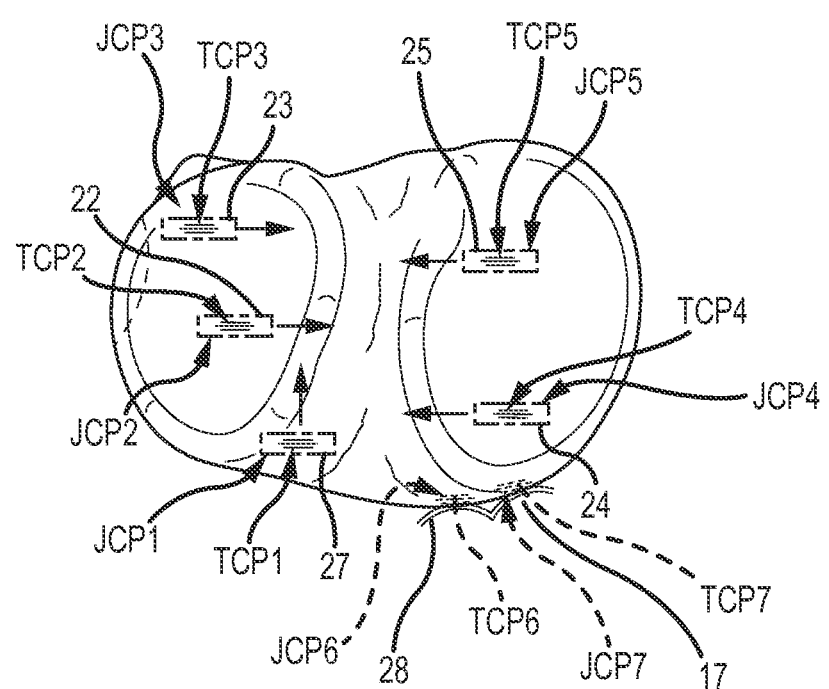
FIG. 6 is a top representative view of a proximal portion of the tibia indicating examples of tibia contact points and also illustrating jig features and jig contact points to hold the jig in the proper orientation.

As illustrated in FIGS. 1A, 1B, and 6, contact points (JCP2 and JCP3) are constrained from medial movement by the slope of the articular surface adjacent the lateral intercondylar tubercle 14A. Similarly, contact points (JCP4 and JCP5) are constrained from lateral movement by the slope of the articular surface adjacent the medial intercondylar tubercle 14B. The contact point that is most anterior, JCP1, is constrained from posterior movement by the distally sloping anterior wall of the tibia adjacent to the tubercles 14A, 14B. Finally, contact points TCP6 and TCP7 help to hold the jig against the plateau 11 by butting against the inwardly sloping wall 19 of the medial condyle 10B, and thus trapping the jig from proximal movement (away from the tibia along the axis A-A). Some or all of the points work in harmony, once the jig is properly seated on the tibia, to hold the jig in place and properly align the jig in order to pin the cut plane guide.

Although the jig implementation illustrated includes seven (7) jig contact points, it is possible to provide a jig with slightly more or slightly fewer contact points. For example, JCP2 and JCP3 might be eliminated, and replaced with a contact point lying therebetweeen, and perhaps with a larger cross section, while still abutting the articular surface adjacent to the lateral intercondylar tubercle 14A. In another example, JCP1 may be eliminated. In yet another example, JCP4 and JCP5 may be eliminated, and replaced with a contact point lying therebetweeen, and perhaps with a larger cross section, while still abutting the articular surface adjacent to the medial intercondylar tubercle 14B. In another example, JCP2 and/or JCP4 may be eliminated. While the jig implementation illustrated includes seven jig contact points, it is possible to provide a jig with slightly more or slightly less contact points. For example, JCP2 might be eliminated. In another example, JCP1 may be shifted medially, and JCP4 eliminated. Additionally, it is possible to move the various points anteriorly or posteriorly relative to the positions indicated. Such movement may depend on damage to the knee being replaced, shape of the trochlear groove, shape of one or both condyles, the size of the tibia, and the type of procedure being performed.

Additionally, it is possible to move the various contact points anteriorly, posteriorly, laterally and/or medially relative to the positions indicated. Such movement may depend on damage to the knee being replaced, shape of the trochlear groove, shape of one or both condyles, the size of the tibia, and the type of procedure being performed. Additionally, one of more points may be defined below the tibial plateau at different locations than TCP 6 and TCP 7. For example, points may be positioned to engage the anterior surface, below the plateau, of the lateral tibial condyle.

Providing a different perspective as illustrated in FIG. 6, which is an axial representative view of the proximal region of the tibia and the jig contact surfaces and associated points, the movement constraints are shown with symbols (arrows encircled) illustrating the constraining directions. FIG. 1A, in contrast, illustrates arrows oriented in the direction where the surfaces are unconstrained where the opposite direction (and possibly other directions) is constrained. There are three contact points (JCP1, JCP6 and JCP7) constrained against posterior movement. In some instances, JCP3 and JCP5 may also be constrained against posterior movement by the superior articular surfaces of the respective condyles at TCP3 and TCP5. Similarly, there are one or two contact points (JCP2 and JCP4) constrained against anterior movement by the superior articular surfaces of the respective condyles at TCP2 and TCP4. Further, some or all of the contact points intercooperate to constrain the jig from any form of anterior or posterior movement or rotation over the tibia, by cooperatively opposing both posterior and anterior movement, respectively.

The jig is also held against rotational movement in the axial plane or twisting or canting off the sagittal plane. For perspective, if the tibial plateau region generally between the tubercles is considered along the axis of the tibia, or relatively close, the contact points JCP1 and JCP2 cooperate with JCP4 to oppose rotational forces in the clockwise direction with the axis as reference. Similarly, the contact point JCP5 cooperates with JCP1 to oppose rotational forces in the counter clockwise direction with the axis as reference. JCP6 and JCP7 also work in conjunction with the other contact points to help prohibit rotation, and to prevent the jig from rotating off the tibia coronally.

Referring primarily to FIG. 6, JCP2 is posteriorly offset from JCP1 by about 22 millimeters (a range of 19-25 millimeters being typical) and JCP4 is posteriorly offset from JCP1 by about 15 millimeters (a range of 12 to 28 millimeters being typical). The measurement being transversely (posteriorly) between a sagittal plane defined through each respective point rather than directly from point to point. Using the same technique, JCP5 is posteriorly offset from JCP4 by about 13 millimeters (a range of 10 to 16 millimeters being typical). JCP3 is posteriorly offset from JCP2 by about 10 millimeters (a range of 7 to 13 millimeters) being typical. In contrast, JCP6 and JCP7 are measured a common transverse plane to a common transverse plane of JCP4 (the most proximate contact point in the implementation shown) and is offset by about 7 millimeters (a range of 4 to 10 millimeters being typical).

The various features discussed and shown herein are but one way to create a jig defining the various jig contact points of interest. In the example shown, the CNC machine tool bits and other cutting mechanisms influence the jig shapes. The various surfaces and jig features, on which the jig contact points are defined, are thus defined in part by requirements of the CNC machine. If the jig were formed in another way, such as through 3D printing, molding, and the like, the jig contact point features and overall jig shape may be different than illustrated although the position and relative location of the jig contact points, depending on the patient, would be substantially the same regardless of the jig manufacturing technique employed.

The embodiment shown contemplates a cut plane guide that is separately pinned to the femur so that the jig may be removed prior to resection. It is possible, however, to fabricate the cutting guide into the body of the jig and form a unified structure where the entirety of the jig is pinned to the femur and stays in place during the resectioning procedure. This embodiment contemplates the jig being of possibly different material (e.g., a sufficient hard polymer to receive a saw blade in the cut slot, or stainless steel). It is also possible, depending on the material used for the jig, to place a liner within the cut slot of the cutting guide, where the liner is stainless steel such that the saw will not cut the slot during the back and forth sawing action. It is also possible for the slot to be integrated in the jig directly, in which case the cut plane guide will be a part of the jig.

The embodiment discussed above contemplates the use of pins to secure the jig and the cutting plane guide in place. It is possible, however, to use other forms of anchors such as screws or combinations of screws and pins. It is also possible, in the case of pins, to use some relatively small (smaller than threads of a screw) of some form of abrasive surface—e.g., annular ridges, roughing, or the like along some or all of the pin shaft, to ensure the pins stay in place and therefore holds the respective jig and/or cutting plane guide in place. Moreover, the jig is shown as defining a plurality of apertures, along with respective bosses, to receive such anchors. It is possible, however, to have the apertures defined in separate structures attached to or otherwise associate with the jig or to secure the jig to the femur in some other way, or to simply hold it in place while the cut plane guide is secured to the femur.

While the jig implementation illustrated includes seven jig contact points, it is possible to provide a jig with slightly more or slightly less contact points. For example, JCP2 might be eliminated. In another example, JCP1 may be shifted medially, and JCP4 eliminated. Additionally, it is possible to move the various points anteriorly or posteriorly relative to the positions indicated. Such movement may depend on damage to the knee being replaced, shape of the trochlear groove, shape of one or both condyles, the size of the tibia, and the type of procedure being performed.

The following claims may reference various features of a jig or other structure in relation to various anatomical features of the tibia. Such anatomical features, however, are not intended to form part of the claim.

What is claimed is:

1. A cutting jig for positioning a tibia cutting tool on a tibia including a first and a second intercondylar tubercle with a spine therebetween, a first articular region adjacent the first intecondylar tubercle and a second articular region adjacent the second intercondylar tubercle, the tibia further including a tibia shaft, the cutting jig comprising:
   a substrate including:
      a first jig contact point oriented to contact the tibia anterior of the spine when the jig is positioned on the tibia for a procedure;
      a second jig contact point oriented to contact the first articular region of the tibia when the jig is positioned on the tibia for a procedure;

a third jig contact point oriented to contact the first articular region of the tibia when the jig is positioned on the tibia for a procedure, the second jig contact point proximate the first jig contact point;

a fourth jig contact point oriented to contact the second articular region of the tibia when the jig is positioned on the tibia for a procedure; and a fifth jig contact point oriented to contact the second articular region of the tibia when the jig is positioned on the tibia for a procedure, the fifth jig contact point proximate the fourth jig contact point;

a projection extending from the substrate, the projection including:

a sixth contact point oriented to contact the tibia shaft when the jig is positioned on the tibia for a procedure;

a seventh contact point oriented to contact the tibia shaft when the jig is positioned on the tibia for a procedure, the seventh contact point proximate the sixth contact point; and a cut guide.

2. The cutting jig of claim 1 wherein at the least the first jig contact point is defined on a first curvilinear projection extending from the substrate.

3. The cutting jig of claim 2 wherein the first curvilinear projection defines a planar semi-circle with a first radius, with the jig contact point defined along a discrete portion of the curvilinear projection along the radius.

4. The cutting jig of claim 2 wherein the first jig contact point defined on the first curvilinear projection coincides with a point along a curve coinciding with a magnetic resonance image slice of a portion of the tibia anterior the spine at which the first jig contact point will contact the tibia when the jig is positioned on the tibia for a procedure.

5. The cutting jig of claim 1 wherein the second jig contact point and the third jig contact points are defined on a respective second curvilinear projection extending from the substrate and a respective third curvilinear projection extending from the substrate.

6. The cutting jig of claim 5 wherein the second and third curvilinear projections are substantially parallel and separated by between 7 millimeters and 13 millimeters.

7. The cutting jig of claim 1 wherein the fourth jig contact point and the fifth jig contact points are defined on a respective fourth curvilinear projection and fifth curvilinear projection extending from the substrate.

8. The cutting jig of claim 6 wherein the fourth and fifth curvilinear projections are substantially parallel and separated by between 7 millimeters and 13 millimeters.

9. The cutting jig of claim 1 wherein the sixth jig contact point and the seventh jig contact point are defined a respective sixth curvilinear projection and seventh curvilinear projection extending from the projection, the sixth curvilinear projection and seventh curvilinear projection substantially coplanar.

10. The cutting jig of claim 1 further comprising an elongate sighting projection extending from the substrate between at least the second jig contact point and the fifth jig contact point, the elongate sighting projection substantially aligned with the spine when the jig is being mounted on the tibia.

11. The cutting jig of claim 1 further comprising a cutting guide support extending from the substrate, the cutting guide support positioned to retain a cutting guide defining the cut guide.

12. The cutting jig of claim 11 wherein the cutting guide support comprises at least one member extending from the projection, the at least one member positioned to receive the cutting guide in a position whereby a cutting tool may be guided to resect the tibia in a plane traverse an axis of the tibia.

13. The cutting jig of claim 12 wherein the cut guide is a slot configured to receive a saw to perform a resection of the femur, the slot positioned to orient the saw to cut transverse the axis of the tibia.

14. The cutting jig of claim 1 wherein the first jig contact point defines a radius of at least 3 millimeters.

15. The cutting jig of claim 1 further comprising a plurality of apertures positioned to receive a respective plurality of anchors to secure the jig to the tibia.

16. A cutting jig for positioning a tibia cutting tool on a tibia including a first and a second intercondylar tubercle with a spine therebetween, a first articular region adjacent the first intecondylar tubercle and a second articular region adjacent the second intercondylar tubercle, the tibia further including a tibia shaft, the cutting jig comprising:

a substrate including:

a first jig contact point;

a second jig contact point posteriorly positioned relative to the first jig contact point;

a third jig contact point posteriorly spaced from the second jig contact point;

a fourth jig contact point posteriorly spaced relative to the first jig contact point and medially spaced relative to the second jig contact point; and a fifth jig contact point posteriorly spaced from the fourth jig contact point;

a projection extending from the substrate, the projection including:

a sixth contact point medially spaced from the fourth contact point;

a seventh contact point medially spaced form the fourth contact point and proximate the sixth contact point; and a cut guide.

17. The cutting jig of claim 16 wherein:

the first jig contact point is oriented to contact the tibia anterior of the spine when the jig is positioned on the tibia for a procedure;

the second jig contact point is oriented to contact the first articular region of the tibia when the jig is positioned on the tibia for a procedure;

the third jig contact point is oriented to contact the first articular region of the tibia when the jig is positioned on the tibia for a procedure;

the fourth jig contact point is oriented to contact the second articular region of the tibia when the jig is positioned on the tibia for a procedure; and the fifth jig contact point is oriented to contact the second articular region of the tibia when the jig is positioned on the tibia for a procedure;

a projection extending from the substrate, the projection including:

the sixth contact point is oriented to contact the tibia shaft when the jig is positioned on the tibia for a procedure;

the seventh contact point is oriented to contact the tibia shaft when the jig is positioned on the tibia for a procedure.

18. The cutting jig of claim 16 wherein:

the first jig contact point is spaced about 22 millimeters from the second jig contact point;

the third jig contact point is spaced about 10 millimeters from the second jig contact point;

the fourth jig contact point is spaced about 15 millimeters from the first jig contact point; and the fifth jig contact point is spaced about 13 millimeters from the fourth jig contact point.

19. The cutting jig of claim 18 wherein:

the first jig contact point is defined on a first curvilinear projection extending from the substrate, the first curvilinear projection defines a first planar semi-circle with a first radius, with the first jig contact point defined along a discrete portion of the radius.

20. The cutting jig of claim 19 wherein:

the second jig contact point and the third jig contact point are defined on a respective second curvilinear projection extending from the substrate and a respective third curvilinear projection extending from the substrate, the second and third curvilinear projections are posteriorly separated by between 7 millimeters and 13 millimeters.

21. The cutting jig of claim 20 wherein:

the fourth jig contact point and the fifth jig contact point are defined on a respective fourth curvilinear projection and fifth curvilinear projection extending from the substrate, the fourth and fifth curvilinear projections being substantially parallel, the fourth and fifth curvilinear projections are posteriorly separated by between 7 millimeters and 13 millimeters.

22. A cutting jig for positioning a tibia cutting tool on a tibia including a first and a second intercondylar tubercle with a spine therebetween, a first articular region adjacent the first intecondylar tubercle and a second articular region adjacent the second intercondylar tubercle, the tibia further including a tibia shaft, the cutting jig comprising:

a substrate including:

first means for contacting the tibia anterior of the spine when the jig is positioned on the tibia for a procedure;

second means for contacting the first articular region of the tibia when the jig is positioned on the tibia for a procedure;

third means for contacting the first articular region of the tibia when the jig is positioned on the tibia for a procedure, the second jig contact point spaced apart from the first means;

fourth means for contacting the second articular region of the tibia when the jig is positioned on the tibia for a procedure; and fifth means for contacting the second articular region of the tibia when the jig is positioned on the tibia for a procedure;

sixth means for contacting the tibia shaft when the jig is positioned on the tibia for a procedure;

seventh means for contacting the tibia shaft when the jig is positioned on the tibia for a procedure, the seventh means proximate the sixth means; and means for providing a cutting guide.

* * * * *